(12) United States Patent
Li et al.

(10) Patent No.: US 10,234,407 B2
(45) Date of Patent: Mar. 19, 2019

(54) ENHANCED INTERVENTIONAL CT IMAGING OF CRACKS IN ROCKS DURING HYDRAULIC TESTING

(71) Applicant: Institute of Geology and Geophysics, Chinese Academy of Sciences, Beijing (CN)

(72) Inventors: Shouding Li, Beijing (CN); Zhongming Zhou, Beijing (CN); Xiao Li, Beijing (CN); Jianming He, Beijing (CN); Yanhui Liu, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/025,088

(22) Filed: Jul. 2, 2018

(65) Prior Publication Data
US 2018/0306736 A1    Oct. 25, 2018

Related U.S. Application Data

(63) Continuation of application No. PCT/CN2017/096812, filed on Aug. 10, 2017.

(30) Foreign Application Priority Data

Aug. 12, 2016 (CN) .......................... 2016 1 0663060

(51) Int. Cl.
*G01N 1/38* (2006.01)
*G01N 3/12* (2006.01)
(Continued)

(52) U.S. Cl.
CPC ............. *G01N 23/046* (2013.01); *G01N 1/38* (2013.01); *G01N 3/12* (2013.01); *G01N 3/567* (2013.01);
(Continued)

(58) Field of Classification Search
CPC .. G01T 1/00; G01T 1/16; G01T 1/169; G01T 5/00; G01T 5/02; G01T 7/00; G01T 7/02; G01T 7/08; G01N 1/00; G01N 1/28; G01N 1/286; G01N 1/38; G01N 2001/002; G01N 2001/2893; G01N 3/00; G01N 3/02; G01N 3/08; G01N 3/10; G01N 3/12; G01N 3/30; G01N 3/307; G01N 3/32; G01N 3/36; G01N 3/40; G01N 3/42; G01N 3/56; G01N 3/567; G01N 15/00; G01N 15/02; G01N 15/08; G01N 15/0806; G01N 15/082; G01N 15/0846; G01N 15/088; G01N 2015/0023;
(Continued)

*Primary Examiner* — Anastasia Midkiff
(74) *Attorney, Agent, or Firm* — Maier & Maier, PLLC

(57) ABSTRACT

The present invention improves the precision in observing cracks in rocks during a hydraulic fracturing test, improving a scientific understanding of the regular pattern of development cracks in of hydraulically fractured rocks. The technical solution includes: hydraulically fracturing the rock with aqueous solutions containing an interventional contrast-enhanced agent, forming hydraulically fractured cracks, wherein the difference in a mass attenuation coefficient $\mu/\rho$ of x-rays between the cracks and the rock is improved by the interventional contrast-enhanced agent in the cracks, moreover, the difference in mass energy absorption coefficient $\mu_{en}/\rho$ of x-rays between the cracks and the rock is improved, then the linear attenuation coefficient of the reception of the detector is changed, improving the imaging resolution for hydraulically fractured cracks in the rock.

7 Claims, 1 Drawing Sheet

(51) Int. Cl.
*G01N 3/56* (2006.01)
*G01N 15/00* (2006.01)
*G01N 23/04* (2018.01)
*G01N 23/18* (2018.01)
*G01N 23/046* (2018.01)

(52) U.S. Cl.
CPC .............. *G01N 23/04* (2013.01); *G01N 23/18* (2013.01); *G01N 2015/0034* (2013.01); *G01N 2203/0019* (2013.01); *G01N 2203/0062* (2013.01); *G01N 2203/023* (2013.01); *G01N 2203/0242* (2013.01); *G01N 2203/0647* (2013.01); *G01N 2223/646* (2013.01); *G01N 2291/0289* (2013.01); *G01N 2291/048* (2013.01)

(58) Field of Classification Search
CPC ... G01N 2015/0034; G01N 2015/0038; G01N 2015/0227; G01N 2015/025; G01N 2015/03; G01N 2015/035; G01N 23/00; G01N 23/02; G01N 23/04; G01N 23/046; G01N 23/06; G01N 23/083; G01N 23/18; G01N 2223/00; G01N 2223/03; G01N 2223/04; G01N 2223/041; G01N 2223/30; G01N 2223/309; G01N 2223/311; G01N 2223/319; G01N 2223/321; G01N 2223/40; G01N 2223/402–2223/405; G01N 2223/409; G01N 2223/41; G01N 2223/419; G01N 2203/427; G01N 2203/60; G01N 2203/607; G01N 2203/616; G01N 2203/646; G01N 2203/6462; G01N 2203/649; G01N 2291/01; G01N 2291/015; G01N 2291/02; G01N 2291/023; G01N 2291/0232; G01N 2291/028; G01N 2291/0289; G01N 2291/04; G01N 2291/048; G01N 2291/10; G01N 2291/102; G01N 2291/26; G01N 2291/263; G01N 2291/2638; G01N 2291/269; G01N 2291/2698; G01N 2203/0014; G01N 2203/0016; G01N 2203/0019; G01N 2203/003; G01N 2203/0042; G01N 2203/0048; G01N 2203/0058; G01N 2203/006; G01N 2203/0062; G01N 2203/0064; G01N 2203/0066; G01N 2203/02; G01N 2203/022; G01N 2203/023; G01N 2203/0236; G01N 2203/0242; G01N 2203/025; G01N 2203/0254; G01N 2203/026; G01N 2203/04; G01N 2203/0411; G01N 2203/06; G01N 2203/0641; G01N 2203/0647; G01N 2203/0652; G01V 2210/64; G01V 2210/646
See application file for complete search history.

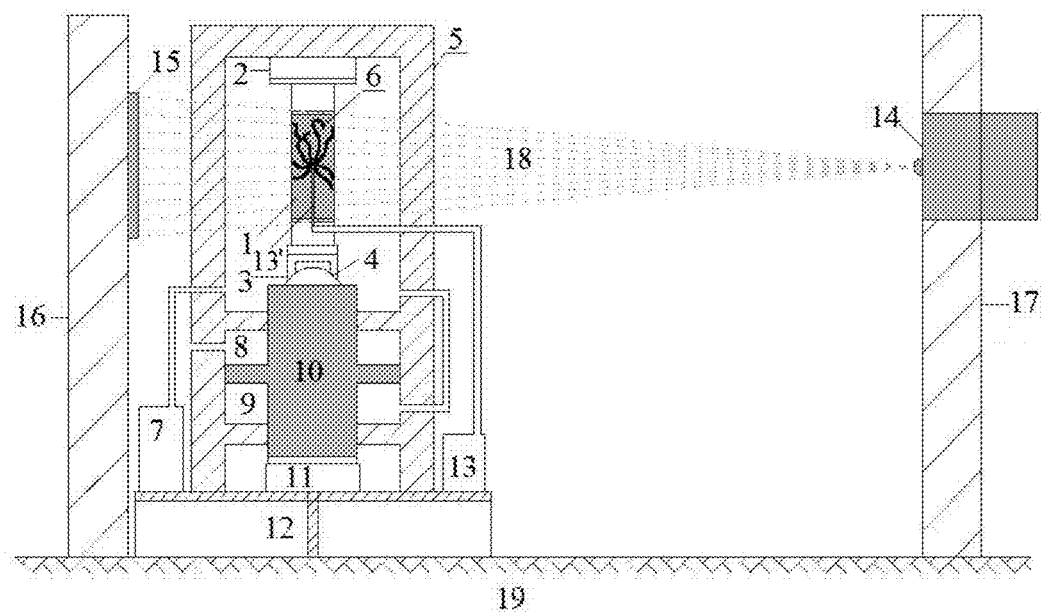

ENHANCED INTERVENTIONAL CT IMAGING OF CRACKS IN ROCKS DURING HYDRAULIC TESTING

FIELD

The present application relates to the technology field of testing the mechanics of rocks.

BACKGROUND

The distribution of fractured cracks is an important measurement of a physical quantity in a hydraulic fracturing test of rocks. Presently, observing cracks in a hydraulic fracturing test of rocks mainly depends on the technology of acoustic emission monitoring and CT imaging with x-rays. The technology of acoustic emission monitoring is extremely useful in acoustic signal acquisition during the fracturing of rocks. However, it has poor precision in retrieving locations of acoustic signals, especially for examining small dimension samples in a laboratory setting, and it is unable to obtain a relatively precise distribution of fractured cracks. In contrast, CT imaging has higher precision in locating fractured cracks, but a low resolution for cracks with average widths, losing information of the distribution of a number of significant cracks.

Therefore, current methods for observing cracks during a hydraulic fracturing test of rocks fail to satisfy the needs of accurately observing the distribution of cracks in said hydraulic fracturing test of rocks.

SUMMARY

The present application provides a method for enhanced interventional imaging for cracks in rocks, which is able to overcome the disadvantages and deficiencies of low precision of prior art technologies in locating the distribution of hydraulically fractured cracks in a rock, and of poor resolution for cracks with regular widths. The present invention improves the precision in observing cracks in rocks during a hydraulic fracturing test, improving a scientific understanding of the regular pattern of development cracks in of hydraulically fractured rocks. The technical solution includes: hydraulically fracturing the rock with aqueous solutions containing an interventional contrast-enhanced agent, forming hydraulically fractured cracks, wherein the difference in a mass attenuation coefficient $\mu/\rho$ of x-rays between the cracks and the rock is improved by the interventional contrast-enhanced agent in the cracks, moreover, the difference in mass energy absorption coefficient $\mu_{en}/\rho$ of x-rays between the cracks and the rock is improved, then the linear attenuation coefficient of the reception of the detector is changed, improving the imaging resolution for hydraulically fractured cracks in the rock.

The primary technical solution of the method for enhanced interventional imaging for cracks in a hydraulic fracturing test of rocks includes 3 parts: an industrial x-ray CT in a laboratory setting, a hydraulic fracturing testing machine for rocks and a loading and fracturing process of an interventional contrast-enhanced agent. The industrial x-ray CT includes a detector post 16 and a detector 15 thereon, an x-ray source post 17 and an x-ray source 14 thereon, a high precision rotary platform 12, etc. An x-ray 18 emitted from the x-ray source 14 penetrates the rock sample 1, the x-rays after penetration are received by the detector 15, then a CT image is formed based on a distribution $\mu(x, y)$ of a linear attenuation coefficient; the hydraulic fracturing testing machine for rocks includes a rock sample 1, an upper spacer 2, a lower spacer 3, a spherical pedestal 4, a triaxial cylinder 5, a peripheral pressuring pump 7, an upper cavity 8 of a self-balancing piston, a lower cavity 9 of a self-balancing piston, a self-balancing piston 10, and an axial actuator 11, etc., wherein the hydraulic fracturing testing machine is disposed on the high precision rotary platform 12, the rock sample 1 is disposed between the upper spacer 2 and the lower spacer 3, the spherical pedestal 4 reduces the end face effect of the rock sample 1 when loading, the triaxial cylinder 5 and the peripheral pressuring pump 7 implement peripheral pressure loading for the rock sample 1, and the upper cavity 8 of the self-balancing piston, the lower cavity 9 of the self-balancing piston, the self-balancing piston 10 and the axial actuator 11 ensure the implementation of axial loading for the rock sample 1, when the hydraulic fracturing testing machine for rocks is loaded for peripheral pressure, axial compression and hydraulic fracturing, the rotary platform 12 rotates at a certain rate; the loading and fracturing process of an interventional contrast-enhanced agent is characterized in that: first, formulating an interventional contrast-enhanced agent for cracks at a certain concentration, wherein the interventional contrast-enhanced agent is a nanogold aqueous solution at a concentration of 5000 ppm containing a dispersant, the particle diameters of the nanogold is 12-5 nm, secondly, fracturing the rock sample 1 to form fractured cracks 6 in the rock sample 1, by pressing the interventional contrast-enhanced agent into the rock sample 1 via the high pressure water pump containing the interventional contrast-enhanced agent.

Fundamental Principle and Technology

A CT image of x-rays penetrating a rock reflects a resorption level of x-rays in various positions of the rock, where a mineral density in the rock is proportional to an x-ray resorption coefficient, the higher an atomic number in the mineral is, the more evident an x-ray attenuation is, and the greater a mass attenuation coefficient is. The larger the difference between adjacent mineral densities is, the greater a contrast of CT imaging of x-rays is, and the higher a resolution is. Utilizing this principle, a method for enhanced interventional CT imaging for hydraulically fractured cracks in rocks is provided, which improves the resolution in imaging hydraulically fractured cracks, and is characterized by using a nanoscale metallic element with high atomic number to affect the process of x-ray projection by way of the method for enhanced interventional imaging which increases a difference in a mass attenuation coefficient $\mu/\rho$ between different substances, and increases a difference in a mass energy absorption coefficient $\mu_{en}/\rho$ between different substances. The difference in attenuation coefficients between the water in the fractured cracks and the rock is relatively small, the contrast of CT imaging for rocks is small, the resolution is low, and the attenuation coefficient of the liquid of metallic powder is higher than the attenuation coefficient of the rock, and when using a liquid of nano metallic powder to replace the original fluid in the cracks, the contrast difference of the linear attenuation coefficient of the detector reception becomes larger, and then the imaging resolution of hydraulic fractured cracks in rocks is further improved.

The primary technical solution of the method for enhanced interventional imaging for cracks in a hydraulic fracturing test of rocks consists of 3 parts: an industrial x-ray CT in a laboratory setting, a hydraulic fracturing testing machine for rocks, and a loading and fracturing process of an interventional contrast-enhanced agent.

The industrial x-ray CT is characterized by consisting of apparatuses including a detector post 16 and a detector 15 thereon, an x-ray source post 17 and an x-ray source 14 thereon, a high precision rotary platform 12, etc. An x-ray 18 emitted from the x-ray source 14 penetrates the rock sample 1, the x-rays after penetration are received by the detector 15, then a CT image is formed based on a distribution $\mu(x, y)$ of linear attenuation coefficient.

The hydraulic fracturing testing machine for rocks is characterized by consisting of a rock sample 1, an upper spacer 2, a lower spacer 3, a spherical pedestal 4, a triaxial cylinder 5, a peripheral pressuring pump 7, an upper cavity 8 of a self-balancing piston, a lower cavity 9 of a self-balancing piston, a self-balancing piston 10 and an axial actuator 11, etc., wherein the hydraulic fracturing testing machine is disposed on the high precision rotary platform 12, the rock sample 1 is disposed between the upper spacer 2 and the lower spacer 3, the spherical pedestal 4 reduces the end face effect of the rock sample 1 when loading, the triaxial cylinder 5 and the peripheral pressuring pump 7 implement peripheral pressure loading for the rock sample 1, and the upper cavity 8 of the self-balancing piston, the lower cavity 9 of the self-balancing piston, the self-balancing piston 10 and the axial actuator 11 ensure implementation of axial loading for the rock sample 1, when the hydraulic fracturing testing machine for rocks is loaded for peripheral pressure, axial compression and hydraulic fracturing, the rotary platform 12 rotates at a certain rate.

The loading and fracturing process of an interventional contrast-enhanced agent is characterized in that: first, formulating an interventional contrast-enhanced agent for cracks at a certain concentration, wherein the interventional contrast-enhanced agent is a nanogold aqueous solution at a concentration of 5000 ppm and containing a dispersant, the diameters of the nanogold particles are in a range of 12-15 nm, second, fracturing the rock sample 1 to form fractured cracks 6 in the rock sample 1 by pressing the interventional contrast-enhanced agent into the rock sample 1 via the high pressure water pump containing the interventional contrast-enhanced agent.

BRIEF DESCRIPTION OF DRAWINGS

FIG. 1 is an exemplary diagram showing a system for imaging cracks in a rock, where
1: rock sample;
2: upper spacer;
3: lower spacer;
4: spherical pedestal;
5: triaxial cylinder;
6: fractured cracks;
7: peripheral pressuring pump;
8: upper cavity of self-balancing piston;
9: lower cavity of self-balancing piston;
10: self-balancing piston 10;
11: axial actuator 11;
12: high precision rotary platform;
13: high pressure water pump containing interventional contrast-enhanced agent;
14: x-ray source;
15: detector;
16: detector post;
17: x-ray source post;
18: x-ray beam; and
19: foundation base.

DESCRIPTION OF EMBODIMENTS

First, formulating an interventional contrast-enhanced agent for cracks at a certain concentration: stirring a dispersant with a mass fraction of 5%, a nano bismuth powder with a mass fraction of 20%, and a polyethylene glycol with a mass fraction of 75% for 10 minutes via a high speed rotor instrument, and vibrating them for 30 minutes via an ultrasonic vibrator to obtain a dispersed nano bismuth solution, wherein the diameters of the nano bismuth particles are in a range of 40-50 nm, then adding the interventional contrast-enhanced agent into the high pressure water pump 13.

The hydraulic fracturing testing machine is disposed on the high precision rotary platform 12, the rock sample 1 is disposed between the upper spacer 2 and the lower spacer 3, the spherical pedestal 4 reduces the end face effect of the rock sample 1 when loading, the triaxial cylinder 5 and the peripheral pressuring pump 7 implements peripheral pressure loading for the rock sample 1, and the upper cavity 8 of the self-balancing piston, the lower cavity 9 of the self-balancing piston, the self-balancing piston 10 and the axial actuator 11 ensure implementation of axial loading for the rock sample 1, when the hydraulic fracturing testing machine for rocks is loaded for peripheral pressure, axial compression and hydraulic fracturing, the rotary platform 12 rotates at a certain rate.

Running the industrial x-ray CT in a laboratory setting, an x-ray 18 emitted from the x-ray source 14 penetrates the rock sample 1, the x-rays after penetration are received by the detector 15, and a CT image is formed based on a distribution of linear attenuation coefficient.

Pressing the interventional contrast-enhanced agent into the rock sample 1, fracturing the rock sample 1 to form fractured cracks 6 in the rock sample 1, which are filled with a nanogold aqueous solution, utilizing the principle of the interventional contrast-enhanced agent, which improves the difference in the mass attenuation coefficient $\mu/\rho$ between different substances, i.e., increases the difference in the mass energy absorption coefficient $\mu_{en}/\rho$ between different substances, affecting the process of x-ray projection, to change the linear attenuation coefficient of the reception of the detector 15, and then to improve the imaging resolution of the hydraulically fractured cracks 6 in the rock.

What is claimed is:
1. A system for high precision imaging of cracks in a hydraulic fracturing test of rock, comprising: an industrial x-ray CT in a laboratory setting, a high precision rotary platform and a hydraulic fracturing testing machine for rocks provided on the high precision rotary platform,
wherein the hydraulic fracturing testing machine for rocks includes a support device, a peripheral pressurizing device, an axial pressurizing device and a high pressure water pump, wherein the support device is used for clamping a rock sample to be fractured, the peripheral pressurizing device is disposed to surround the rock sample and used for applying pressure on periphery of the rock sample, the axial pressurizing device is provided below the support device and used for applying axial pressure to the rock sample, and the high pressure water pump is used for delivering interventional contrast-enhanced agent into the rock sample to form cracks within the rock sample,
wherein the industrial x-ray CT is used for forming a CT image of the cracks within the rock sample, wherein the interventional contrast-enhanced agent is a dispersed nano bismuth solution which is made by the following steps: stirring a dispersant with a mass fraction of 5%, a nano bismuth powder with a mass fraction of 20% and a polyethylene glycol with a mass fraction of 75% for a first time period, and vibrating them for a second time period.

2. The system as defined by claim 1, wherein diameters of particles of the nano bismuth material are in the range of 40-50 nm.

3. The system as defined by claim 2, wherein the first time period is 10 minutes, and the second time period is 30 minutes.

4. The system as defined by claim 3, wherein the support device includes an upper spacer and a lower spacer, and the upper spacer and the lower spacer support the rock sample from upper and lower sides of the rock sample respectively.

5. The system as defined by claim 4, wherein the peripheral pressurizing device includes a triaxial cylinder surrounding the rock sample and a peripheral pressurizing pump in communication with the triaxial cylinder, and the peripheral pressurizing pump supplies power for the triaxial cylinder to apply peripheral pressure to the rock sample.

6. The system as defined by claim 5, wherein the axial pressurizing device includes an axial actuator disposed on the high precision rotary platform and a self-balancing piston disposed on the axial actuator, such that the axial actuator applies axial pressure to the rock sample through the self-balancing piston.

7. The system as defined by claim 6, wherein the laboratorial x-ray industrial CT includes an x-ray source and a CT detector, wherein the x-ray source is used for emitting x-rays, wherein the CT detector receives the x-rays that have penetrated the rock sample, and wherein the CT detector uses the received x-rays to form a CT image based on a distribution of linear attenuation coefficients obtained from materials within the rock sample being penetrated by the x-rays.

* * * * *